US008394030B2

(12) United States Patent
Varga et al.

(10) Patent No.: US 8,394,030 B2
(45) Date of Patent: Mar. 12, 2013

(54) EXHALED BREATH CONDENSATE BIOMETRIC MARKER MEASUREMENT APPARATUS AND METHOD

(75) Inventors: Christopher Varga, Mission Viejo, CA (US); Alex Stenzler, Long Beach, CA (US)

(73) Assignee: CareFusion 207, Inc., San Diego, CA (US)

( * ) Notice: Subject to any disclaimer, the term of this patent is extended or adjusted under 35 U.S.C. 154(b) by 424 days.

(21) Appl. No.: 12/406,349

(22) Filed: Mar. 18, 2009

(65) Prior Publication Data

US 2010/0241019 A1 Sep. 23, 2010

(51) Int. Cl.
*A61B 5/08* (2006.01)
*G01N 1/22* (2006.01)
*G01N 31/00* (2006.01)
*G01N 33/497* (2006.01)

(52) U.S. Cl. .......... 600/532; 600/543; 600/529; 73/23.3
(58) Field of Classification Search .......... 600/529–543; 73/23.3
See application file for complete search history.

(56) References Cited

U.S. PATENT DOCUMENTS

| | | | | |
|---|---|---|---|---|
| 6,585,661 | B1 * | 7/2003 | Hunt et al. | 600/532 |
| 7,118,537 | B2 * | 10/2006 | Baddour | 600/543 |
| 7,377,901 | B2 * | 5/2008 | Djupesland et al. | 600/529 |
| 2003/0208132 | A1 * | 11/2003 | Baddour | 600/532 |
| 2004/0127808 | A1 * | 7/2004 | Vaughan et al. | 600/532 |
| 2005/0085739 | A1 * | 4/2005 | MacDonald et al. | 600/530 |
| 2007/0100250 | A1 * | 5/2007 | Kline | 600/532 |
| 2007/0167853 | A1 * | 7/2007 | Melker et al. | 600/532 |
| 2007/0249958 | A1 * | 10/2007 | Martin et al. | 600/551 |
| 2008/0009761 | A1 * | 1/2008 | Acker et al. | 600/532 |
| 2008/0045825 | A1 * | 2/2008 | Melker et al. | 600/365 |
| 2008/0214947 | A1 * | 9/2008 | Hunt et al. | 600/532 |
| 2009/0151479 | A1 * | 6/2009 | Bartel et al. | 73/864.51 |
| 2010/0191138 | A1 * | 7/2010 | Bulbrook | 600/543 |

OTHER PUBLICATIONS

Cepkova, Magda et al., "Biological markers of lung injury before and after the institution of positive pressure ventilation in patients with acute lung injury", Critical Care, vol. 10, No. 5, (2006), pp. 1-8.
Sznajder, J. Iasha et al., "Increased Hydrogen Peroxide in the Expired Breath of Patients With Acute Hypoxemic Respiratory Failure", American College of Physicians, Chest Journal, Sep. 4, 2008, pp. 606-612.

* cited by examiner

*Primary Examiner* — Navin Natnithithadha
*Assistant Examiner* — Sunita Reddy
(74) *Attorney, Agent, or Firm* — McDermott Will & Emery LLP

(57) ABSTRACT

The present invention includes an apparatus and a method for testing exhaled breath condensate for at least one biometric marker, including a substrate for collecting exhaled breath condensate, the substrate capable of being brought to a temperature below a dew point of vapor in exhaled breath, a collector for retaining the substrate and for receiving a biometric marker reagent. The invention may further include receiving exhaled breath in a collector, the collector comprising a substrate, the substrate being at a temperature below a dew point of vapor in exhaled breath, collecting the exhaled breath condensate on the substrate, and bringing a biometric marker reagent in contact with the substrate.

5 Claims, 2 Drawing Sheets

EXHALED BREATH CONDENSATE BIOMETRIC MARKER MEASUREMENT APPARATUS AND METHOD

FIELD OF THE INVENTION

The present invention relates to an apparatus and method for testing exhaled breath condensate for pulmonary biometric markers.

BACKGROUND OF THE INVENTION

It is generally known that exhaled breath contains certain useful biometric markers which may be used to determine whether a patient has a particular illness. For example, elevated levels of interleukin-6, interleukin-8, intercellular adhesion molecule-1 (ICAM-1), and von Willebrand factor (vWF) may indicate that a patient has an acute lung injury. See Cepkova, Magda et al., "Biological markers of lung injury before and after the institution of positive pressure ventilation in patients with acute lung injury," http://ccforum.com/content/10/5/R126, Critical Care 2006, 10:R126 doi:10.1186/cc5037, Sep. 6, 2006 (accessed Feb. 24, 2009).

Although exhaled breath is primarily gaseous (i.e., air), there is a moisture content in the breath which can be collected in liquid form and separated from the gaseous components. This moisture content in the aforementioned exhaled breath may be collected as condensate when it accumulates on a surface, similarly to when someone breathes on a mirror. This condensate is known as "exhaled breath condensate." It is possible to collect the exhaled breath condensate from a patient and test it to determine whether a particular biometric marker is present.

Conventional exhaled breath condensate testing devices and methods are designed to collect a large sample of condensate, typically over a 10-20 minute breathing period. This long collection time period is required to allow for enough condensate to be collected to provide for transfer to pipettes, test tubes, slides, or other typical laboratory testing apparatuses, requiring even more time for diagnosis.

In accordance with conventional methods and apparatuses, the patient must breathe into a device, and the condensate collects on a surface, which may be a flat surface or in a collection device, e.g., a test tube. The collected sample is then typically taken to a laboratory for analysis, which is oftentimes off-site if the collection is performed in a patient's home or in a doctor's office where there is typically no in-house laboratory. Therefore, for conventional devices and methods, the time required from breath collection to diagnosis and the patient's receiving results may be hours, days, or even weeks.

This may be problematic if immediate confirmation of an injury or illness is required, and significantly slows down the process of diagnosing a patient. Moreover, the conventional devices and methods must be used under professional supervision, and are not available for home use by a patient.

Accordingly, there is a need and desire for an exhaled breath condensate testing device that is easy to use and gives rapid results.

SUMMARY OF THE INVENTION

Embodiments of the present invention advantageously provide an apparatus and method for simple rapid exhaled breath condensate testing.

In one embodiment, an apparatus for testing exhaled breath condensate for at least one biometric marker includes a substrate for collecting breath condensate, the substrate capable of being brought to a temperature below the dew point of vapor in exhaled breath, and a collector for retaining the substrate and for receiving a biometric marker reagent. The collector includes an actuator for bringing the biometric marker reagent in contact with the substrate.

In another embodiment, a method of testing exhaled breath condensate for at least one biometric marker includes receiving exhaled breath in a collector, the collector comprising a substrate, the substrate being at a temperature below the dew point of vapor in exhaled breath, collecting the exhaled breath condensate on the substrate, and activating an actuator to bring a biometric marker reagent in contact with the substrate.

In yet another embodiment, an apparatus for testing exhaled breath condensate for at least one biometric marker includes a means for collecting exhaled breath condensate. The means for collecting includes a means for retaining a substrate, the substrate capable of being brought to a temperature below the dew point of vapor in exhaled breath, a means for receiving a biometric marker reagent, and a means for bringing said biometric marker reagent in contact with said substrate.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

Figure 1:
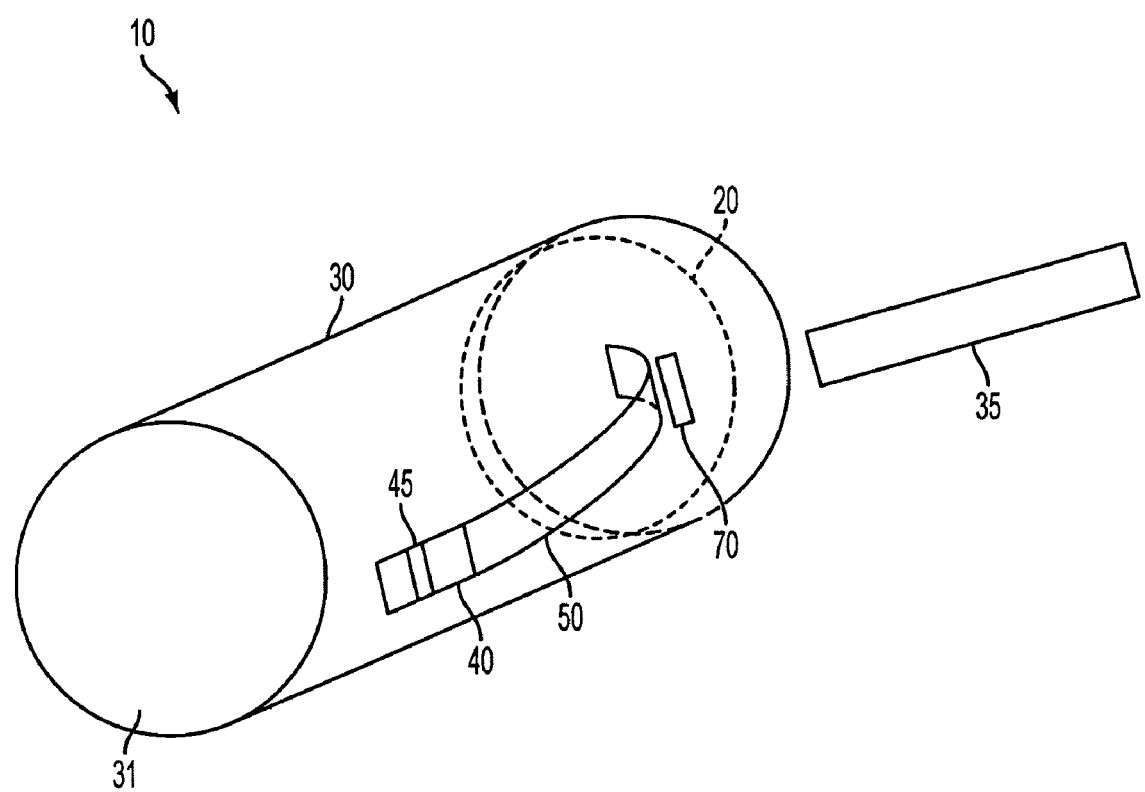
FIG. 1 is a schematic diagram of an embodiment of the present invention.

In the following detailed description, reference is made to the accompanying drawings, which form a part hereof and show by way of illustration specific embodiments in which the invention may be practiced. These embodiments are described in sufficient detail to enable those skilled in the art to practice them, and it is to be understood that other embodiments may be utilized, and that structural, logical, processing, and electrical changes may be made. The progression of processing steps described is an example; however, the sequence of steps is not limited to that set forth herein and may be changed as is known in the art, with the exception of steps necessarily occurring in a certain order.

The invention will now be described with reference to the drawing figures, in which like reference numerals refer to like parts throughout.

FIG. 1 is a schematic view of an embodiment of the present invention. An apparatus 10 for testing exhaled breath condensate for at least one biometric marker, generally designated 10, is depicted in FIG. 1. The apparatus 10 for testing exhaled breath condensate includes a substrate 20 for collecting a test sample of exhaled breath condensate, and a collector 30 for retaining the substrate 20 and for receiving a biometric marker reagent. The aforementioned biometric marker reagent is typically conveyed on a biometric marker reagent strip 35. The substrate 20 is capable of being brought to a temperature below the dew point of vapor in exhaled breath, typically below 0° C.

Although the apparatus for testing exhaled breath condensate 10 depicted in FIG. 1 as a cylindrical tube, the shape of the collector 30 may have varying geometries and/or shapes. For instance, the collector 30 may be an elongated tube attached to a receptacle. The collector 30 should have a breath opening 31 for receiving breath from the patient. The breath opening 31 may receive the breath directly, e.g., by the patient's putting his or her mouth directly on the breath opening 31, or indirectly by an additional mouthpiece (not shown) or breathing tube (not shown).

Similarly, the substrate 20 is not limited to the illustrated cylindrical shape, but may be any shape or geometry appropriate to collect the exhaled breath condensate. For example, the substrate 20 may be flat at the bottom of a tube, or bent or curved to extend into the collector 30. As further example, the substrate 20 may be concave, as in a bowl shape, convex, spherical, smooth, rough, or corrugated. The geometry of the substrate 20 may also be dependent on desired surface area. The substrate 20 may be any material suitable for cooling to a temperature below the dew point of vapor in exhaled breath. For example, and without limitation, any metal (e.g., aluminum), ceramic, ceramic on metal, glass, or multilayer material may be used. In one preferred embodiment, the substrate 20 comprises a material which does not interfere or react with the biometric marker to be tested.

In one preferred embodiment of the present invention, the collector 30 includes an optional actuator 40. The actuator 40 functions to bring the biometric marker reagent strip 35 into contact with the substrate 20. The actuator 40 may include a button 45, as shown in FIG. 1 as a slide button. The actuator 40 is not limited to a slide button 45, but may be any suitable mechanical or electromechanical device or the like which allows the reagent strip 35 to come into contact with the substrate 20.

The actuator 40 may further include a contact 50, which is configured to press the reagent strip 35 against the surface of the substrate 20 on which the exhaled breath condensate has formed. The actuator 40 also may function to slide the reagent strip 35 across a surface of the substrate 20 on which the exhaled breath condensate has formed. Such sliding may be in any suitable direction.

It should be noted, however, that the actuator 40, along with the associated button 45 and contact 50 are optional, and the device may operate in any suitable manner where the biometric marker reagent is brought into contact with the condensate on the substrate 20. For example, a user may manually contact the biometric marker reagent or any suitable reagent-bearing material (e.g., biometric marker reagent strip 35) to the exhaled breath condensate on the substrate 20.

The biometric marker reagent may take various designs and/or forms. For example, if the biometric marker reagent is on a biometric marker reagent strip 35, as depicted in FIG. 1, the biometric marker reagent strip 35 may be a calorimetric reagent strip or material. During operation of the testing apparatus 10, the color of the strip or material may change. The degree and nature of the change may depend on the presence or concentration of the associated biometric marker in the test sample.

The change in reagent color may be monochromatic, i.e., an intensity of color, or may be a change over a color spectrum. For example, if litmus is the reagent, it turns a deeper red at a higher pH (i.e., acid), and blue for lower pH (i.e., base). Another example of a pH indicator is universal indicator, which has the following ranges and outputs. For pH 0-3, which is a strong acid, the color is red. For pH 3-6, which is an acid, the color is orange to yellow as the concentration decreases (i.e., weaker acid). For pH 7, which is neutral, the color is green. For pH 8-11, which is an alkali (i.e., base), the color is blue. For pH 11-14, which is a strong alkali (i.e., strong base), the color is purple. Other biometric marker reagents may use different color schemes.

The aforementioned changing of colors of the biometric marker reagent strip 35 allows the operator, e.g., a doctor or the patient, to visually compare the color result to a reference or chart to quickly analyze the result. The strip may also be subjected to a reader (not shown) that would give a digital, image, and/or text output to the operator (e.g., a doctor or the patient). For example, such a reader may analyze the color or another indicator made by the biometric marker reagent to output a number indicating a concentration of the detected biometric marker, or a YES/NO type, i.e., binary result (as is known for pregnancy tests), or some other appropriate text or image for displaying a result.

The reagent strip 35 may be a single-use reagent strip or a multiple-use reagent strip. If it is a multiple-use reagent strip, it may be, for example, a roll of reagent-treated material, which may be attached to or fed into the collector 30. The material may be fed, whether single-use or multiple-use, into the collector 30 via an opening 70, which may extend through the collector from outside to inside, or may be concealed within the body of the collector 30 so that the material is stored in a compartment within the collector 30. It should also be appreciated that the opening 70 may be of any suitable geometry, including a guiding path for guiding the reagent-bearing material onto the substrate 20.

The biometric marker reagent may test for any biometric marker found in exhaled breath condensate, including, but not limited to, pH, hydrogen peroxide ($H_2O_2$), protein, lactate, glucose, ketone, ammonia, nitric oxide (NO), nitrogen dioxide ($NO_2$), toxic metal, chlorine, interleukin-6, interleukin-8, cytokine, surfactant protein D (SP-D), soluble tumor necrosis factor receptor (sTNFR), tumor necrosis factor receptor (TNFR), intercellular adhesion molecule-1 (ICAM-1), and von Willebrand factor (vWF).

Figure 2:
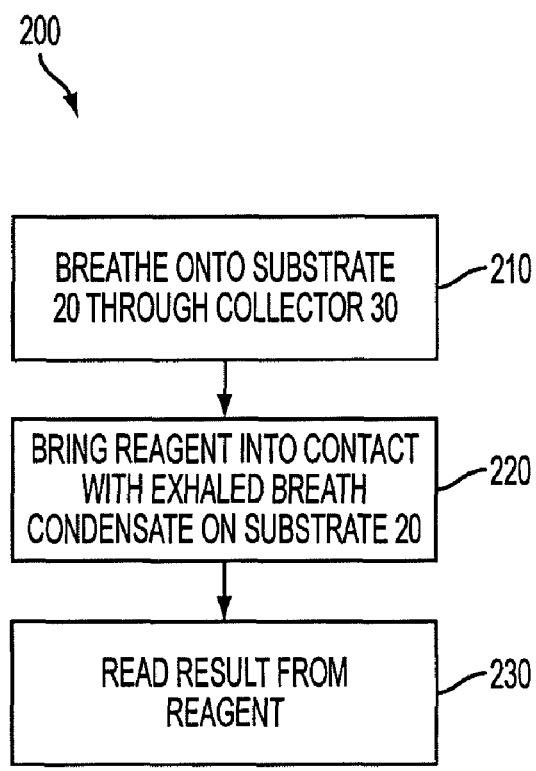
FIG. 2 is a flow chart of a method in accordance with an embodiment of the invention.

FIG. 2 is a flow chart of a method 200 in accordance with an embodiment of the present invention. During operation, a patient (not shown) exhales a breath into the collector 30 (step 210), and as the breath contacts the substrate, moisture or condensate in the exhaled breath collects on the substrate 20, which is at a temperature below the dew point of vapor in the exhaled breath. This may be as few as two or three breaths from the patient, which may require less than a minute. Since the substrate 20 is chilled below the dew point of vapor in the exhaled breath, the condensate easily forms.

Referring now to step 220, the biometric marker reagent, which is depicted in FIG. 1 as being conveyed on the biometric marker reagent strip 35, is brought into contact with the condensate collected on the substrate 20. The contact may be produced by pressing the reagent against the surface of the substrate 20 containing the condensate or by sliding the reagent against the surface of the substrate 20. In one preferred embodiment, the forementioned pressing or sliding action can be accomplished by using the optional actuator 40 and the associated button 45 and contact 50.

An operator, whether the patient or another, may get a resultant biometric marker from the reagent's processing within seconds, depending upon the inherent processing time of the particular reagent (step 230). Therefore, the time period for receiving a result for a biometric marker associated with said biometric marker reagent may be as short as a combination of the time to collect the exhaled breath from the patient, the time to bring the reagent into contact with the exhaled breath, and the inherent time required for the reagent to process the test sample.

It should be noted that the substrate may be brought below the dew point of vapor in exhaled breath by any suitable method or device. For example, it may be stored in a refrigeration device, such as a refrigerator or freezer. The entire apparatus 10 may be cooled, or any portion thereof, so long as the substrate is cooled. As such, the present invention may be suitable for use by the patient in his or her home or place of business, or wherever the substrate 20 may be transported and cooled to monitor his or her own health without requiring a trained professional to be present. It is also possible to pre-cool the substrate 20 and transport it with the patient to provide additional portability and convenience.

It should further be appreciated that the substrate 20 may be self-cooled, such as an electric cold plate, or it may contain a material that provides cooling, such as a chemical which may participate in an endothermic reaction to cool the surface of the substrate 20. The collector 30 may also include such a chemical, chemical receptacle, or refrigeration device. This may provide additional convenience and/or portability.

The processes and devices in the above description and drawings illustrate examples of methods and devices of many that could be used and produced to achieve the objects, features, and advantages of embodiments described herein. Thus, they are not to be seen as limited by the foregoing description of the embodiments, but only limited by the appended claims. The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

What is claimed is:

1. An apparatus that tests exhaled breath condensate for at least one biometric marker, the apparatus comprising:
    a substrate that collects exhaled breath from a user to produce exhaled breath condensate after said substrate is brought to a temperature below a dew point of vapor in said exhaled breath; and
    a collector that retains said substrate such that said substrate occupies an inner surface area less than a whole of said inner surface area of said collector, said exhaled breath condensate is at least formed at said substrate, said collector further receiving a biometric marker reagent strip such that said biometric marker reagent strip comes into contact with said exhaled breath condensate disposed on a surface of said substrate such that a result of said contact is indicated at an end of a first time period, and said collector further comprises:
        a first opening that receives said exhaled breath from said user, wherein said first opening is a hole that is shaped to receive a person's mouth surrounding said first opening such that said person's mouth completely covers said first opening when said means for collecting exhaled breath condensate is receiving said exhaled breath;
        a second opening that receives a material there through, said material containing said biometric marker reagent strip, wherein said second opening is one of a hole that extends through said means for collecting exhaled breath condensate and a hole that is concealed within the body of said means for collecting exhaled breath condensate, a circumference of said hole being of a geometry that is suitable for receiving said material of a particular size and shape, and wherein said second opening is positioned at an end portion of said means for collecting exhaled breath condensate, wherein said end portion is on an opposite side of said means for collecting exhaled breath condensate as said first opening; and
    an actuator that brings said biometric marker reagent strip in contact with said substrate.

2. The apparatus of claim 1, wherein said actuator presses said biometric marker reagent strip against a surface of said substrate.

3. The apparatus of claim 1, wherein said actuator slides said biometric marker reagent strip across a surface of said substrate.

4. The apparatus of claim 1, wherein during said third time period an actuator is operated, said actuator bringing said biometric marker reagent strip in contact with said substrate.

5. An apparatus that tests exhaled breath condensate for at least one biometric marker, said apparatus comprising:
    a means for collecting exhaled breath condensate, said means for collecting comprising:
        a first opening for receiving exhaled breath from a user, wherein said first opening is a hole that is shaped to receive a person's mouth surrounding said first opening such that said person's mouth completely covers said first opening when said means for collecting exhaled breath condensate is receiving said exhaled breath; and
    a retaining means for retaining a substrate by a collector, said substrate collecting said exhaled breath to produce said exhaled breath condensate after said substrate is brought to a temperature below a dew point of vapor in exhaled breath, said collector retaining said substrate such that said substrate occupies an inner surface area less than a whole of said inner surface area of said collector, said exhaled breath condensate is at least formed at said substrate;
    a receiving means for receiving a biometric marker reagent strip such that said biometric marker reagent strip comes into contact with a surface of said substrate and said exhaled breath condensate disposed thereon, said receiving means comprising:
        a second opening for receiving a material there through, said material containing said biometric marker reagent strip, wherein said second opening is one of a hole that extends through said means for collecting exhaled breath condensate and a hole that is concealed within the body of said means for collecting exhaled breath condensate, a circumference of said hole being of a geometry that is suitable for receiving said material of a particular size and shape, and wherein said second opening is positioned at an end portion of said means for collecting exhaled breath condensate, wherein said end portion is on an opposite side of said means for collecting exhaled breath condensate as said first opening; and
    an actuator means for bringing said biometric marker reagent strip in contact with said substrate.

* * * * *